United States Patent
Huo et al.

(10) Patent No.: US 7,747,052 B2
(45) Date of Patent: Jun. 29, 2010

(54) SYSTEM AND METHOD FOR DETECTING SOLID COMPONENTS OF GROUND GLASS NODULES IN PULMONARY COMPUTED TOMOGRAPHY IMAGES

(75) Inventors: Jing Huo, Los Angeles, CA (US); Li Zhang, Skillman, NJ (US); Carol L. Novak, Newtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 909 days.

(21) Appl. No.: 11/555,817

(22) Filed: Nov. 2, 2006

(65) Prior Publication Data

US 2007/0122078 A1    May 31, 2007

Related U.S. Application Data

(60) Provisional application No. 60/740,415, filed on Nov. 29, 2005.

(51) Int. Cl.
  *G06K 9/00* (2006.01)
  *A61B 6/00* (2006.01)

(52) U.S. Cl. .......................... 382/128; 378/21

(58) Field of Classification Search ................. 382/128, 382/129, 130, 131, 132, 133, 134, 164, 171, 382/173, 179; 378/4, 21, 22, 23, 24, 25, 378/26, 27, 901; 424/9.4
See application file for complete search history.

(56) References Cited

U.S. PATENT DOCUMENTS

| | | | |
|---|---|---|---|
| 6,937,776 B2 * | 8/2005 | Li et al. | ..................... 382/260 |
| 2005/0254697 A1 | 11/2005 | Zhang et al. | |
| 2006/0120585 A1 | 6/2006 | Zhang et al. | |

OTHER PUBLICATIONS

Feng Li, MD, PhD, et al., "Malignant versus Benign Nodules at CT Screening for Lung Cancer: Comparison of Thin-Section CT Findings," Radiology (2004) 233:793-798.

Zhang Li, et al., "A Computer-based Method of Segmenting Ground Glass Nodules in Pulmonary CT Images: Comparison to Expert Radiologists' Interpretations," In Proc. SPIE Medical Imaging, Image Processing (j. Michael Fitzpatrick and Joseph M. Reinhardt, eds.) vol. 5747 pp. 113-121 (2005).

* cited by examiner

*Primary Examiner*—Abolfazl Tabatabai

(57) ABSTRACT

A method for detecting solid components in ground glass nodules (GGNs) in medical images, includes: performing an intensity-based segmentation on a segmented GGN to identify a high intensity region; and performing a shape analysis to determine whether the high intensity region is a solid component or a vessel, wherein the shape analysis comprises: computing a compactness of the high intensity region; and determining whether the high intensity region is a solid component or a vessel by using an area, a maximum distance on a distance transform map and the compactness of the region; or determining whether the high intensity region is a solid component or a vessel by scaling and normalizing the region and computing a compactness for the scaled and normalized region.

22 Claims, 6 Drawing Sheets

Solid Nodule     Pure Ground Glass Nodule (GGN)     Mixed GGN

SYSTEM AND METHOD FOR DETECTING SOLID COMPONENTS OF GROUND GLASS NODULES IN PULMONARY COMPUTED TOMOGRAPHY IMAGES

CROSS-REFERENCE TO RELATED APPLICATION

This application claims the benefit of U.S. Provisional Application No. 60/740,415, filed Nov. 29, 2005, a copy of which is herein incorporated by reference.

BACKGROUND OF THE INVENTION

1. Technical Field

The present invention relates to the detection and evaluation of ground glass nodules (GGNs) in medical images, and more particularly, to a system and method for detecting solid components of GGNs in pulmonary computed tomography (CT) images.

2. Discussion of the Related Art

With the widespread availability of multi-slice computed tomography (CT) scanners for lung cancer screening and the ever-improving resolution offered by these scanners, an increasing number of small pulmonary nodules are being detected at their early stages for cancer diagnosis.

Lung nodules can be classified into solid nodules and ground glass nodules (GGNs). GGNs can be further grouped into pure GGNs that contain only non-solid (e.g., low-density) elements and mixed GGNs that contain both solid and non-solid components. Solid nodules, pure GGNs and mixed GGNs have different appearances in pulmonary CT images as shown in FIG. 1.

In Feng Li, Shusuke Sone, Hiroyuki Abe, Heber MacMahon and Kunio Doi, "Malignant versus Benign Nodules at CT Screening for Lung Cancer: Comparison of Thin Section CT Findings", Radiology 2004 233: 793-798, it was shown that GGNs are more likely to be associated with malignancy than solid nodules. The ratio of a solid component to an entire GGN is an important indicator for nodule characterization.

Accordingly, there is a need for a solid component detection method that is capable of providing fast and consistent measures for cancer diagnosis and treatment.

SUMMARY OF THE INVENTION

In an exemplary embodiment of the present invention, a method for detecting solid components in ground glass nodules (GGNs) in medical images, comprises: performing an intensity-based segmentation on a segmented GGN to identify a high intensity region; and performing a shape analysis to determine whether the high intensity region is a solid component or a vessel, wherein the shape analysis comprises: computing a compactness of the high intensity region; and determining whether the high intensity region is a solid component or a vessel by using an area, a maximum distance on a distance transform map and the compactness of the region; or determining whether the high intensity region is a solid component or a vessel by scaling and normalizing the region and computing a compactness for the scaled and normalized region.

Performing an intensity-based segmentation comprises: applying a high threshold to the segmented GGN to identify pulmonary structures having high intensity; and after the high threshold has been applied, applying a low threshold to the segmented GGN to include boundary voxels that belong to the pulmonary structures having high intensity. Computing a compactness of the high intensity region comprises: computing a compactness of the region in 2D; and computing a compactness of the region in 3D.

Determining whether the high intensity region is a solid component or a vessel by using an area, a maximum distance on a distance transform map and the compactness of the region comprises labeling the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

The method further comprises setting a value of at least one of the first area, first through third distances and first through third compactnesses. The compactness of the scaled and normalized region identifies the scaled and normalized region as a solid component or a vessel. The method further comprises acquiring a pulmonary image including a non-segmented GGN by using a computed tomography (CT) technique and segmenting the non-segmented GGN.

In an exemplary embodiment of the present invention, a system for detecting solid components in GGNs in medical images, comprises: a memory device for storing a program; and a processor in communication with the memory device, the processor operative with the program to: perform an intensity-based segmentation on a segmented GGN to identify a high intensity region; and perform a shape analysis to determine whether the high intensity region is a solid component or a vessel, wherein when performing the shape analysis the processor is further operative with the program to: compute a compactness of the high intensity region; and determine whether the high intensity region is a solid component or a vessel by using an area, a maximum distance on a distance transform map and the compactness of the region; or determine whether the high intensity region is a solid component or a vessel by scaling and normalizing the region and computing a compactness for the scaled and normalized region.

When performing an intensity-based segmentation the processor is further operative with the program to: apply a high threshold to the segmented GGN to identify pulmonary structures having high intensity; and after the high threshold has been applied, apply a low threshold to the segmented GGN to include boundary voxels that belong to the pulmonary structures having high intensity. When computing a compactness of the high intensity region the processor is further operative with the program to: compute a compactness of the region in 2D; and compute a compactness of the region in 3D.

When determining whether the high intensity region is a solid component or a vessel by using an area, a maximum distance on a distance transform map and the compactness of the region the processor is further operative with the program to label the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

The processor is further operative with the program to set a value of at least one of the first area, first through third distances and first through third compactnesses. The compactness of the scaled and normalized region identifies the scaled and normalized region as a solid component or a vessel. The processor is further operative with the program to acquire a pulmonary image including a non-segmented CGN from a CT scanner and segment the non-segmented GGN.

In an exemplary embodiment of the present invention, a method for detecting solid components in GGNs in medical images, comprises: performing an intensity-based segmentation on a segmented volume of interest (VOI) to identify a high intensity region, wherein the VOI includes a GGN; performing a shape analysis to determine whether the high intensity region is a solid component of the GGN or a vessel, wherein the shape analysis comprises: computing a compactness of the high intensity region; and determining whether the high intensity region is a solid component of the GGN or a vessel by using an area, a maximum distance on a distance transform map and the compactness of the region; or determining whether the high intensity region is a solid component of the GON or a vessel by scaling and normalizing the region and computing a compactness for the scaled and normalized region.

Performing an intensity-based segmentation comprises: applying a high threshold to the segmented VOI to identify pulmonary structures having high intensity; and after the high threshold has been applied, applying a low threshold to the segmented VOI to include boundary voxels that belong to the pulmonary structures having high intensity.

Determining whether the high intensity region is a solid component of the GGN or a vessel by using an area, a maximum distance on a distance transform map and the compactness of the region comprises labeling the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

The compactness of the scaled and normalized region identifies the scaled and normalized region as a solid component or a vessel.

In an exemplary embodiment of the present invention, a system for detecting solid components in GGNs in medical images, comprises: a memory device for storing a program; and a processor in communication with the memory device, the processor operative with the program to: perform an intensity-based segmentation on a segmented VOI to identify a high intensity region, wherein the VOI includes a GGN; perform a shape analysis to determine whether the high intensity region is a solid component of the GGN or a vessel, wherein when performing the shape analysis the processor is further operative with the program to: compute a compactness of the high intensity region; and determine whether the high intensity region is a solid component of the GGN or a vessel by using an area, a maximum distance on a distance transform map and the compactness of the region; or determine whether the high intensity region is a solid component of the GGN or a vessel by scaling and normalizing the region and computing a compactness for the scaled and normalized region.

When performing an intensity-based segmentation the processor is further operative with the program to: apply a high threshold to the segmented VOI to identify pulmonary structures having high intensity; and after the high threshold has been applied, apply a low threshold to the segmented VOI to include boundary voxels that belong to the pulmonary structures having high intensity.

When determining whether the high intensity region is a solid component of the GGN or a vessel by using an area, a maximum distance on a distance transform map and the compactness of the region the processor is further operative with the program to label the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

The compactness of the scaled and normalized region identifies the scaled and normalized region as a solid component or a vessel.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 1:
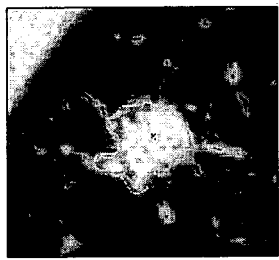
FIG. 1 is a set of images illustrating a solid nodule, a pure ground glass nodule (GGN) and a mixed GGN.
Figure 1:
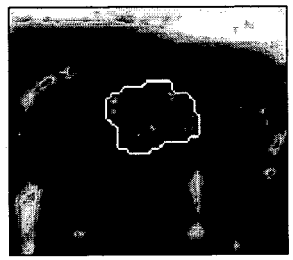
Figure 1:
Figure 2:
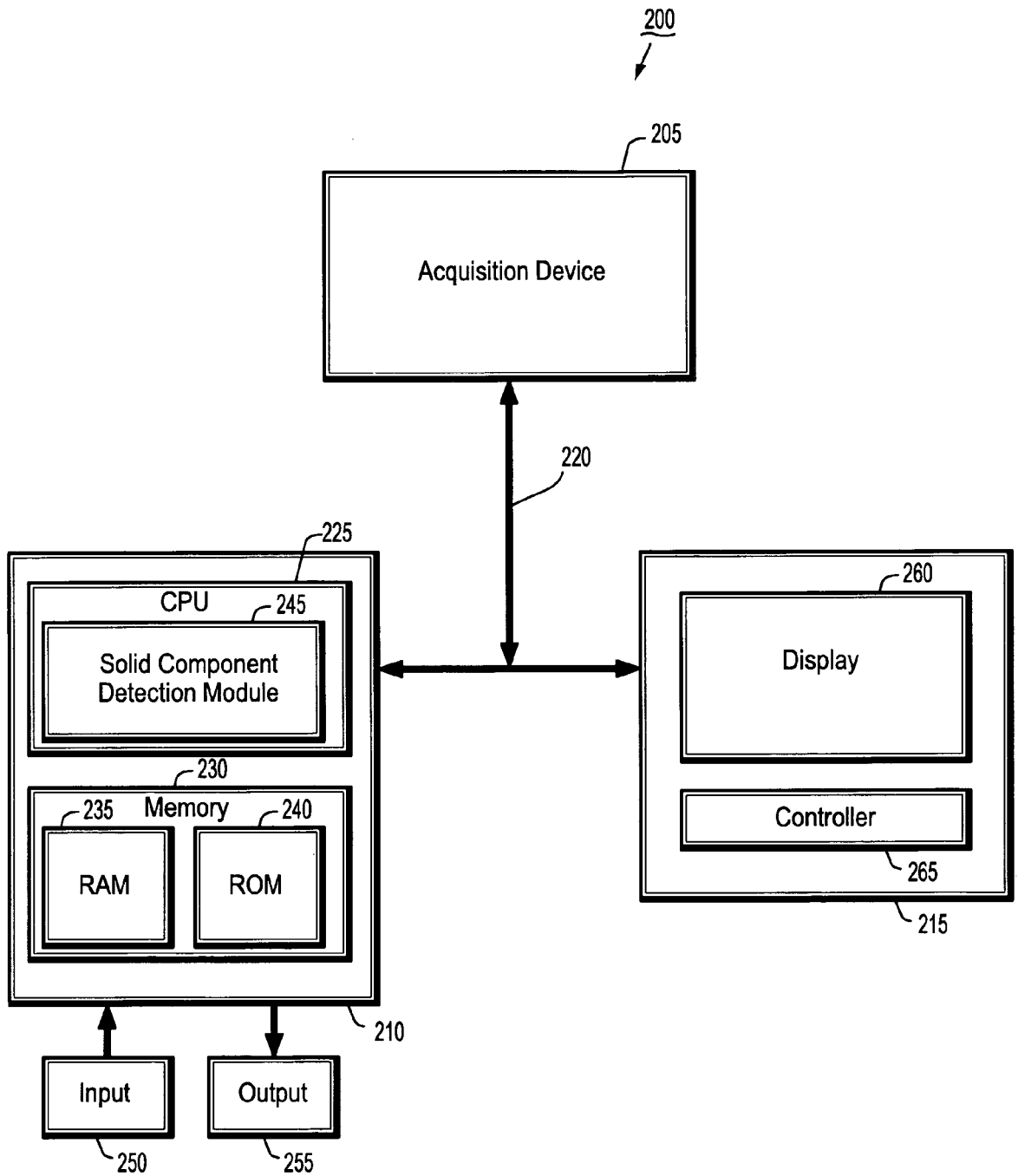
FIG. 2 is a block diagram illustrating a system for detecting solid components of GGNs in pulmonary computed tomography (CT) images according to an exemplary embodiment of the present invention.

FIG. 2 is a block diagram illustrating a system 2 for detecting solid components of ground glass nodules (GGNs) in pulmonary computed tomography (CT) images according to an exemplary embodiment of the present invention. As shown in FIG. 2, the system 200 includes an acquisition device 205, a PC 210 and an operator's console 215 connected over a wired or wireless network 220.

The acquisition device 205 may be a CT imaging device or any other 3D high-resolution imaging device such as a magnetic resonance (MR) scanner.

The PC 210, which may be a portable or laptop computer, a medical diagnostic imaging system or a picture archiving communications system (PACS) data management station, includes a CPU 225 and a memory 230 connected to an input device 250 and an output device 255. The CPU 225 includes a solid component detection module 245 that includes one or more methods for detecting solid components of GGNs in pulmonary CT images to be discussed hereinafter with reference to FIGS. 3-6. Although shown inside the CPU 225, the solid component detection module 245 can be located outside the CPU 225.

The memory 230 includes a RAM 235 and a ROM 240. The memory 230 can also include a database, disk drive, tape drive, etc., or a combination thereof, The RAM 235 functions as a data memory that stores data used during execution of a program in the CPU 225 and is used as a work area. The ROM 240 functions as a program memory for storing a program executed in the CPU 225. The input 250 is constituted by a keyboard, mouse, etc., and the output 255 is constituted by an LCD, CRT display, printer, etc.

The operation of the system 200 can be controlled from the operator's console 215, which includes a controller 265, e.g., a keyboard, and a display 260. The operator's console 215 communicates with the PC 210 and the acquisition device 205 so that image data collected by the acquisition device 205 can be rendered by the PC 210 and viewed on the display 260. The PC 210 can be configured to operate and display information provided by the acquisition device 205 absent the operator's console 215, by using, e.g., the input 250 and output 255 devices to execute certain tasks performed by the controller 265 and display 260.

The operator's console 215 may further include any suitable image rendering system/tool/application that can process digital image data of an acquired image dataset (or portion thereof) to generate and display images on the display 260. More specifically, the image rendering system may be an application that provides rendering and visualization of medical image data, and which executes on a general purpose or specific computer workstation. The PC 210 can also include the above-mentioned image rendering system/tool/application.

Figure 3:
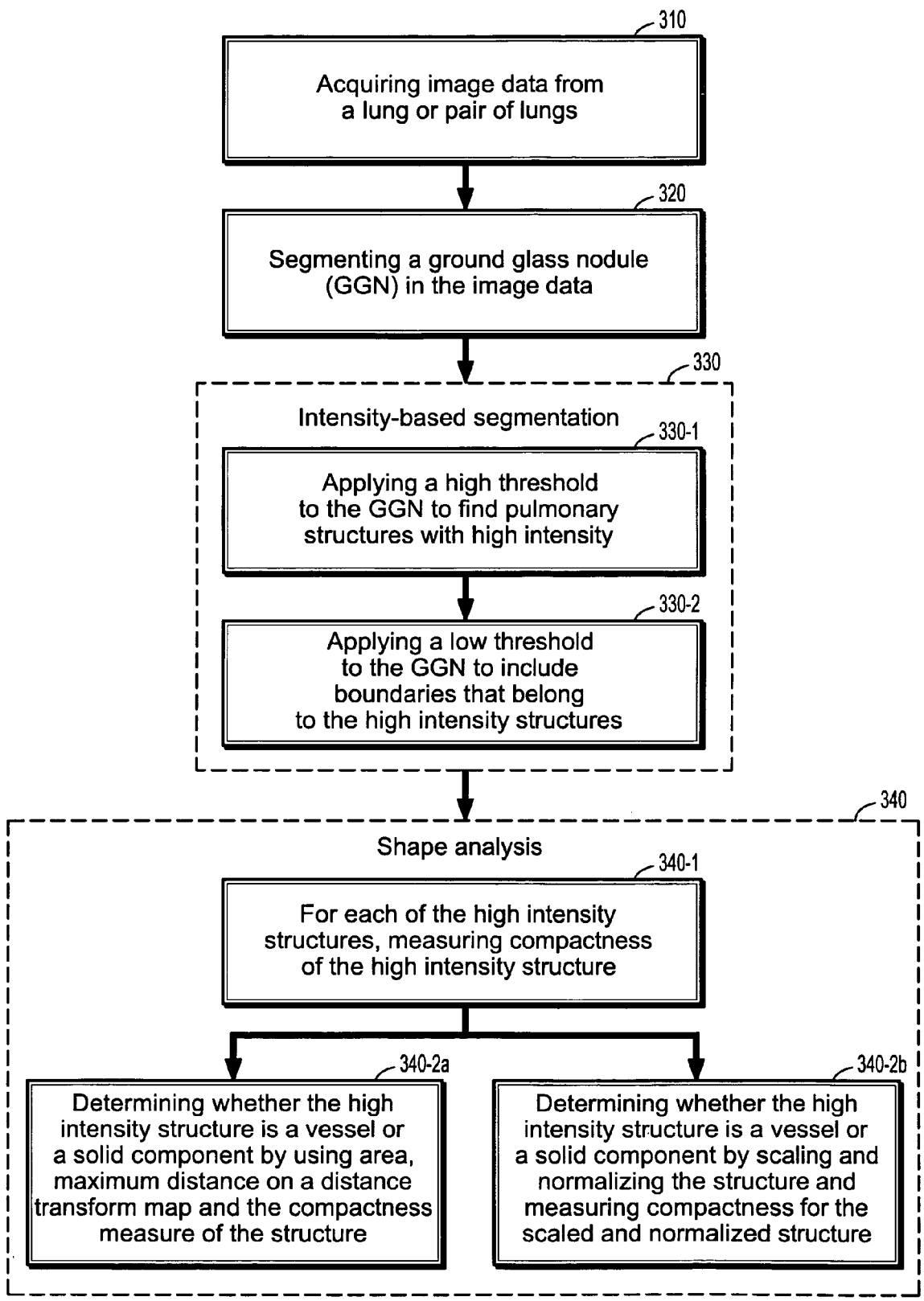
FIG. 3 is a flowchart illustrating a method for detecting solid components of GGNs in pulmonary CT images according to an exemplary embodiment of the present invention.

FIG. 3 is a flowchart illustrating a method for detecting solid components of GGNs in pulmonary CT images according, to an exemplary embodiment of the present invention. As shown in FIG. 3, image data is acquired from a lung or pair of lungs of a patient (310). This is accomplished, e.g., by using the acquisition device 205, which in this example is a CT scanner operated at the operator's console 215, to scan the patient's chest thereby generating a series of 2D image slices associated with the chest. The 2D image slices are then combined to form a 3D image of the lungs.

After the 3D image data of the lungs is acquired, a GGN in the image data is segmented (320). The GGN may be segmented by using a variety of techniques including but not limited to the technique described in Li Zhang, Tiantian Zhang, Carol L. Novak, David P. Naidich and Daniel A. Moses, "A computer-based method of segmenting ground glass nodules in pulmonary CT images. comparison to expert radiologists' interpretations", in Proc. SPE Medical Imaging, image Processing, (J. Michael Fitzpatrick and Joseph M. Reinhardt, eds.), vol. 5747, pp. 113-121, 2005, a copy of which is incorporated by reference herein in its entirety.

Briefly, the computer-based method is initialized by a click point and uses a Markov random field (MRF) model for segmentation. While the intensity distribution varies for different GGNs, the intensity model used in the MRF is adapted for each nodule based on initial estimates.

Once the GGN is segmented, an intensity-based segmentation is performed to find high intensity structures and/or regions in the image data (330). In the intensity-based segmentation, regions with high intensity, which are solid component candidates, are identified using a two-step thresholding method described, e.g., in U.S. Patent Application Publication Nos. 20050254697 and 20060120585, copies of which are incorporated by reference herein in their entirety.

Figure 4:
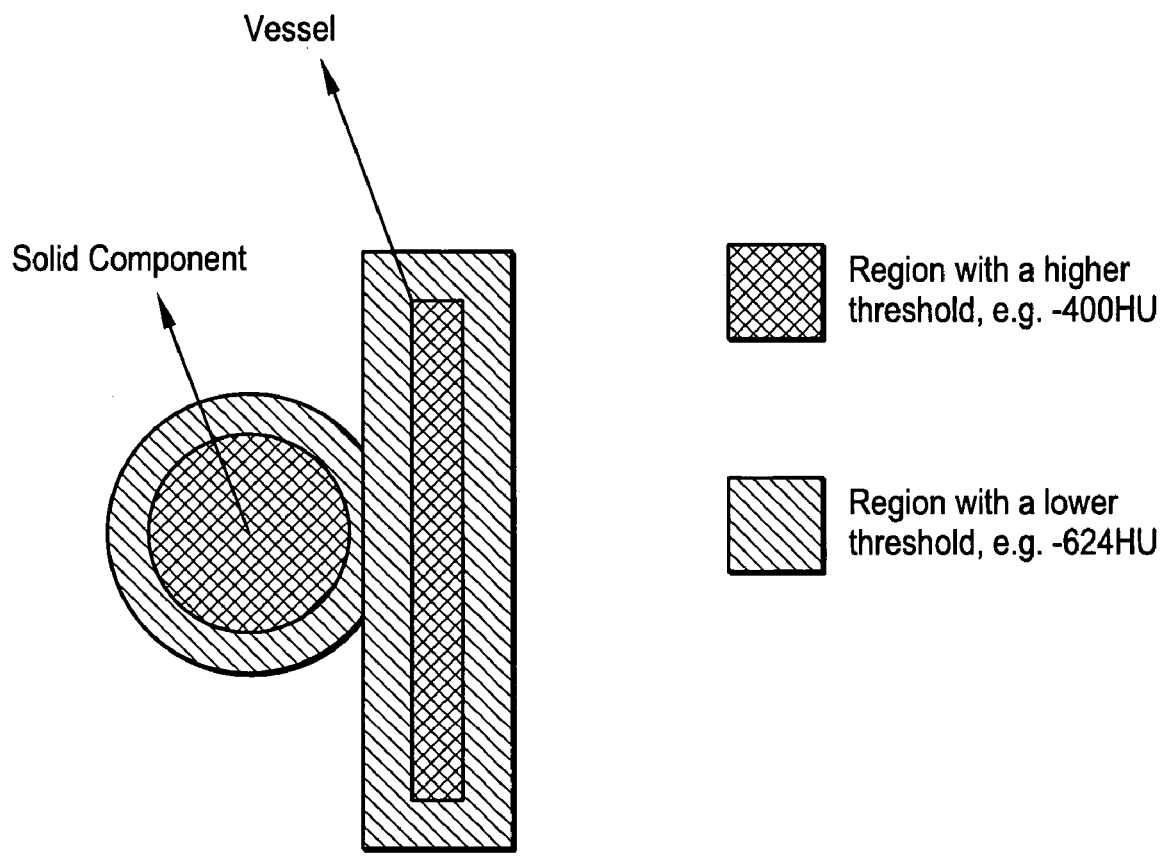
FIG. 4 is a diagram illustrating a two-step thresholding for use with an exemplary embodiment of the present invention.

In this two-step thresholding approach illustrated in FIG. 4, a high threshold (e.g., −400HU) is first used to find pulmonary structures with high intensity (330-1). Due to a partial volume effect, boundary voxels that belong to these structures are not included. Thus, to include these boundary voxels and complete the segmentation, a lower threshold (e.g., −624HU) is then applied (330-2).

It is to be understood that if a lower threshold is used in the first step to find high intensity regions, lung parenchyma might erroneously be included, thereby connecting different high intensity regions. In this case, separate anatomic structures with high intensity cannot be distinguished (as shown in FIG. 4). Thus, a high threshold is used in the first step to identify different anatomic structures with high intensity, and once an individual structure is identified, a lower threshold can be used to get a complete segmentation $O_{all}$.

To include the boundary voxels in the high intensity region segmentation, a dilation constrained by intensity is used to get the complete segmentation $O_{all}$ as follows:

$$O_{all} = O_{core} \cup \{\bar{x} | \bar{x} \in (O_{core} \oplus SE - O_{core}) \text{ and } I_{\bar{x}} \geq T_{low}\} \quad \text{Equation 1}$$

where $O_{core}$ is a core part of the segmentation obtained from the identification step using a higher threshold, $T_{high}$. $\oplus$ denotes morphological dilation, and SE is the dilation structure element (e.g., a 3×3 cube). $I_{\bar{x}}$ is the intensity value at location $\bar{x}$ and $T_{low}$ is the lower threshold used to complete the segmentation.

Now that the intensity-based segmentation is complete, a shape analysis performed on the high-intensity regions (340). This is done to determine whether the segmented high intensity regions are solid components or vessels. Compactness of a high intensity region is used to distinguish vessels from solid components since tube shaped vessel branches are less compacted than solid components of GGNs. In the shape analysis step 340, a 2D and 3D compactness of each of the high intensity regions is considered (340-1).

The compactness of a high intensity region is defined as:

$$2D: \text{ compactness} = \frac{P * P}{4\pi A}, \quad \text{Equation 2}$$

where P is the perimeter and A is the area of the 2D region; and $$3D: \text{ compactness} = \frac{V}{\frac{4}{3}\pi d_m^3}, \quad \text{Equation 3}$$

where V is the volume of the 3D region, and $d_m$ is the maximum value of a distance transform map of the 3D region (e.g., similar to the maximum radius).

According to the above definitions, the compactness of a 2D or 3D sphere should be 1. A less compact region, such as a long tube-like vessel branch, should have a compactness value much larger than 1, while a sphere-like solid component should have a value close to T.

However, in the digital domain, due to the limitation of the definition given in Equations 2 and 3, the compactness value varies for the same shape with different sizes. In light of this, a multi-thresholding (340-2a) or a scaling and normalization (340-2b) are performed.

In the multi-thresholding step 340-2a, an area of the high intensity region, maximum value on a distance transform map of the high intensity region and the compactness measure of the high intensity region are considered to determine whether the high intensity region is a vessel or a solid component. A high intensity region will be labeled a vessel if:

(Area>$^{T_{a1}}$ pixels) and

[(Maximum Distance<$^{d_1}$) and (compactness>$^{C_1}$) or (Maximum Distance<$^{d_2}$) and (compactness>$^{C_2}$) or (Maximum Distance<$^{d_3}$) and (compactness>$^{C_3}$)].

Here, $T_{a1}$ is set to 10 initially, and can be fine-tuned experimentally during implementation, Similarly, $d_1, d_2, d_3, C_1, C_2, C_3$ can be initially set as: $d_1=7, d_2=11, d_3=16, C_1=10, C_2=24, C_3=34$, and fine-tuned during implementation. These multiple thresholds compensate for the fact that in a digital image, the compactness value is not independent of magnification.

In the scaling and normalization step 340-2b, the high intensity region is scaled and normalized to a standard size. A compactness measure is then computed based on the normalized size. In this case, the disparity of the original and re-computed compactness values caused by the size difference for the same shape is eliminated and only one compactness threshold is needed.

Figure 5A:
FIG. 5A is an image illustrating solid component detection according to an exemplary embodiment of the present invention performed only within a GGN segmentation wherein a vessel was erroneously segmented as a solid component.

It is to be understood that if solid component detection is performed only within a GGN segmentation, it may he difficult to differentiate solid components from any vessel that runs through a GGN since only parts of such vessels may be included in an initial GGN segmentation. These vessel portions may have compactness values that are similar to the compactness values of solid components. Thus, as shown in FIG. 5A, a vessel (indicated by the inner contour of FIG. 5A) of a GGN (indicated by the outer contour of FIG. 5A) can be erroneously detected as a solid component of the GGN.

Figure 5B:
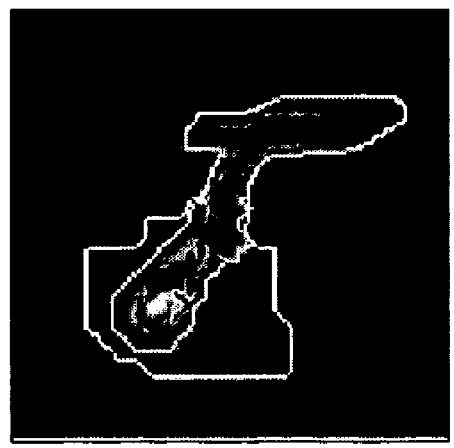
FIG. 5B is an image illustrating correct detection of the vessel of FIG. 5A by performing solid component detection according to an exemplary embodiment of the present invention within a volume of interest (VOI)

However, in FIG. 5B, by applying the intensity-based segmentation in the area of a volume of interest (VOI) (indicated by the outer contour in FIG. 5B) instead of limiting it to the region included in the GGN segmentation (indicated by the inner contour in FIG. 5B), a complete segmentation of the vessel can be obtained, and then, the vessel can be removed from the GGN segmentation. Once the vessel has been removed, solid components can be detected within the GGN segmentation.

Figure 6:
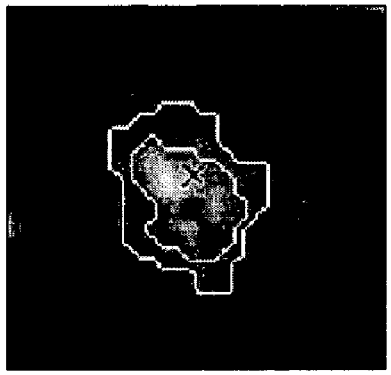
FIG. 6 is a pair of images illustrating results obtained from segmenting two mixed GGNs according to an exemplary embodiment of the present invention.
Figure 6:
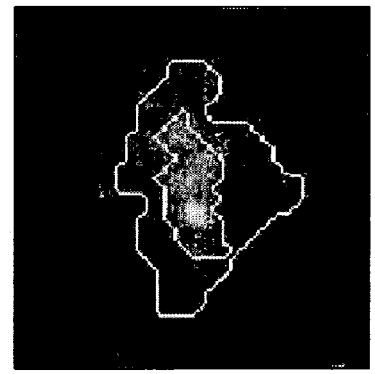

FIG. 6 illustrates an example of two mixed GGNs segmented according to an exemplary embodiment of the present invention. In particular, these GGNs underwent the above-described two-step segmentation process followed by a compactness measure. As shown in FIG. 6, the inner contours show the automatically computed solid component, while the outer contours show the result for the whole GGN.

In accordance with an exemplary embodiment of the present invention, a technique for detecting solid components in automatically segmented GGNs is provided. In this approach, an intensity-based segmentation is first used, and then, shape analysis using compactness and distance transform is applied to distinguish solid components from vessels. By using this technique, solid components in GGNs can be automatically detected, thereby enabling fast and consistent measures for cancer diagnosis and treatment.

It should to be understood that the present invention may he implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for detecting solid components in ground glass nodules (GGNs) in medical images, comprising:
   performing an intensity-based segmentation on a segmented GGN to identify a high intensity region; and
   performing a shape analysis to determine whether the high intensity region is a solid component or a vessel, wherein the shape analysis comprises:
   computing a compactness of the high intensity region; and
   determining whether the high intensity region is a solid component or a vessel by using an area, a maximum distance on a distance transform map and the compactness of the region; or
   determining whether the high intensity region is a solid component or a vessel by scaling and normalizing the region and computing a compactness for the scaled and normalized region.

2. The method of claim 1, wherein performing an intensity-based segmentation comprises:
   applying a high threshold to the segmented GGN to identify pulmonary structures having high intensity; and
   after the high threshold has been applied, applying a low threshold to the segmented GGN to include boundary voxels that belong to the pulmonary structures having high intensity.

3. The method of claim 1, wherein computing a compactness of the high intensity region comprises:
   computing a compactness of the region in 2D; and
   computing a compactness of the region in 3D.

4. The method of claim 1, wherein determining whether the high intensity region is a solid component or a vessel by using an area, a maximum distance on a distance transform map and the compactness of the region comprises:
   labeling the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

5. The method of claim 4, further comprising:
setting a value of at least one of the first area, first through third distances and first through third compactnesses.

6. The method of claim 1, wherein the compactness of the scaled and normalized region identifies the scaled and normalized region as a solid component or a vessel.

7. The method of claim 1, further comprising:
acquiring a pulmonary image including a non-segmented GGN by using a computed tomography (CT) technique; and
segmenting the non-segmented GGN.

8. A system for detecting solid components in ground glass nodules (GGNs) in medical images, comprising:
a memory device for storing a program; and
a processor in communication with the memory device, the processor operative with the program to:
perform an intensity-based segmentation on a segmented GGN to identify a high intensity region; and
perform a shape analysis to determine whether the high intensity region is a solid component or a vessel, wherein when performing the shape analysis the processor is further operative with the program to:
compute a compactness of the high intensity region; and
determine whether the high intensity region is a solid component or a vessel by using an area, a maximum distance on a distance transform map and the compactness of the region; or
determine whether the high intensity region is a solid component or a vessel by scaling and normalizing the region and computing a compactness for the scaled and normalized region.

9. The system of claim 8, wherein when performing an intensity-based segmentation the processor is further operative with the program to:
apply a high threshold to the segmented GGN to identify pulmonary structures having high intensity; and
after the high threshold has been applied, apply a low threshold to the segmented GGN to include boundary voxels that belong to the pulmonary structures having high intensity.

10. The system of claim 8, wherein when computing a compactness of the high intensity region the processor is further operative with the program to:
compute a compactness of the region in 2D; and
compute a compactness of the region in 3D.

11. The system of claim 8, wherein when determining whether the high intensity region is a solid component or a vessel by using an area, a maximum distance on a distance transform map and the compactness of the region the processor is further operative with the program to:
label the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

12. The system of claim 11, wherein the processor is further operative with the program to:
set a value of at least one of the first area, first through third distances and first through third compactnesses.

13. The system of claim 8, wherein the compactness of the scaled and normalized region identifies the scaled and normalized region as a solid component or a vessel.

14. The system of claim 8, wherein the processor is further operative with the program to:
acquire a pulmonary image including a non-segmented GGN from a computed tomography (CT) scanner; and
segment the non-segmented GCN.

15. A method for detecting solid components in ground glass nodules (GGNs) in medical images, comprising:
performing an intensity-based segmentation on a segmented volume of interest (VOI) to identify a high intensity region, wherein the VOI includes a GGN;
performing a shape analysis to determine whether the high intensity region is a solid component of the GGN or a vessel, wherein the shape analysis comprises:
computing a compactness of the high intensity region; and
determining whether the high intensity region is a solid component of the GGN or a vessel by using an area, a maximum distance on a distance transform nap and the compactness of the region; or
determining whether the high intensity region is a solid component of the GGN or a vessel by scaling and normalizing the region and computing, a compactness for the scaled and normalized region.

16. The method of claim 15, wherein performing an intensity-based segmentation comprises:
applying a high threshold to the segmented VOI to identify pulmonary structures having high intensity; and
after the high threshold has been applied, applying a low threshold to the segmented VOI to include boundary voxels that belong to the pulmonary structures having high intensity.

17. The method of claim 15, wherein determining whether the high intensity region is a solid component of the GGN or a vessel by using an area, a maximum distance on a distance transform map and the compactness of the region comprises:
labeling the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

18. The method of claim 15, wherein the compactness of the scaled and normalized region identifies the scaled and normalized region as a solid component or a vessel.

19. A system for detecting solid components in ground glass nodules (GGNs) in medical images, comprising:
a memory device for storing a program; and
a processor in communication with the memory device, the processor operative with the program to:
perform an intensity-based segmentation on a segmented volume of interest (VOI) to identify a high intensity region, wherein the VOI includes a GGN;
perform a shape analysis to determine whether the high intensity region is a solid component of the GGN or a vessel, wherein when performing the shape analysis the processor is further operative with the program to;
compute a compactness of the high intensity region; and
determine whether the high intensity region is a solid component of the GGN or a vessel by using an area, a maximum distance on a distance transform map and the compactness of the region; or
determine whether the high intensity region is a solid component of the GGN or a vessel by sealing and normalizing the region and computing a compactness for the scaled and normalized region.

20. The system of claim 19, wherein when performing an intensity-based segmentation the processor is further operative with the program to:
apply a high threshold to the segmented VOI to identify pulmonary structures having high intensity; and
after the high threshold has been applied, apply a low threshold to the segmented VOI to include boundary voxels that belong to the pulmonary structures having high intensity.

21. The system of claim 19, wherein when determining whether the high intensity region is a solid component of the GGN or a vessel by using an area, a maximum distance on a distance transform map and the compactness of the region the processor is further operative with the program to:
label the region as a vessel if its area is greater than a first area and the maximum distance is less than a first distance and the compactness is greater than a first compactness, or the maximum distance is less than a second distance and the compactness is greater than a second compactness, or the maximum distance is less than a third distance and the compactness is greater than a third compactness.

22. The system of claim 19, wherein the compactness of the scaled and normalized region identifies the scaled and normalized region as a solid component or a vessel.

* * * * *